(12) United States Patent
Nakajima

(10) Patent No.: US 7,008,404 B2
(45) Date of Patent: Mar. 7, 2006

(54) INDWELLING CATHETER

(75) Inventor: Hiroaki Nakajima, Tokyo (JP)

(73) Assignee: Medikit Co., Ltd., Bunkyo-ku (JP)

( * ) Notice: Subject to any disclaimer, the term of this patent is extended or adjusted under 35 U.S.C. 154(b) by 279 days.

(21) Appl. No.: 10/094,662

(22) Filed: Mar. 12, 2002

(65) Prior Publication Data

US 2002/0128604 A1 Sep. 12, 2002

(30) Foreign Application Priority Data

Mar. 12, 2001 (JP) ............................ P2001-068570

(51) Int. Cl.
*A61M 5/178* (2006.01)
(52) U.S. Cl. .................... 604/158; 604/167.02
(58) Field of Classification Search ............... 604/905, 604/249, 246, 158, 523, 160–162, 164.01, 604/164.02, 167.02–167.04, 537; 251/149.1, 251/149.6
See application file for complete search history.

(56) References Cited

U.S. PATENT DOCUMENTS

| | | | |
|---|---|---|---|
| 4,387,879 A * | 6/1983 | Tauschinski | 251/149.1 |
| 4,512,766 A * | 4/1985 | Vailancourt | 604/167.03 |
| 4,917,668 A * | 4/1990 | Haindl | 604/167.03 |
| 5,108,380 A * | 4/1992 | Herlitze et al. | 604/533 |
| 5,215,538 A * | 6/1993 | Larkin | 604/249 |
| 5,350,363 A | 9/1994 | Goode et al. | |
| 5,390,898 A * | 2/1995 | Smedley et al. | 251/149.6 |
| 5,405,323 A * | 4/1995 | Rogers et al. | 604/508 |
| 5,456,675 A * | 10/1995 | Wolbring et al. | 604/537 |
| 5,458,640 A | 10/1995 | Gerrone | |
| 5,584,808 A | 12/1996 | Healy | |
| 5,599,305 A | 2/1997 | Hermann et al. | |
| 5,613,663 A * | 3/1997 | Schmidt et al. | 251/149.2 |
| 5,735,826 A * | 4/1998 | Richmond | 604/251 |
| 5,749,861 A * | 5/1998 | Guala et al. | 604/249 |
| 5,817,069 A * | 10/1998 | Arnett | 604/256 |
| 5,911,710 A | 6/1999 | Barry et al. | |
| 5,954,313 A * | 9/1999 | Ryan | 251/149.1 |
| 5,954,698 A * | 9/1999 | Pike | 604/167.03 |
| 5,967,490 A * | 10/1999 | Pike | 251/149.1 |
| 6,039,302 A * | 3/2000 | Cote et al. | 251/149.1 |
| 6,152,900 A * | 11/2000 | Mayer | 604/167.02 |
| 6,245,048 B1 * | 6/2001 | Fangrow et al. | 604/249 |
| 6,299,131 B1 * | 10/2001 | Ryan | 251/149.1 |
| 6,575,960 B1 * | 6/2003 | Becker et al. | 604/533 |
| 6,585,229 B1 * | 7/2003 | Cote et al. | 251/149.1 |
| 6,595,981 B1 * | 7/2003 | Huet | 604/523 |
| 6,699,221 B1 * | 3/2004 | Vaillancourt | 604/167.01 |
| 2002/0002351 A1 * | 1/2002 | Cote et al. | 604/247 |
| 2002/0013556 A1 * | 1/2002 | Cote et al. | 604/247 |
| 2002/0029020 A1 * | 3/2002 | Cote et al. | 604/247 |

* cited by examiner

*Primary Examiner*—Cris Rodriguez
(74) *Attorney, Agent, or Firm*—Smith Patent Office

(57) ABSTRACT

An indwelling catheter has a hollow catheter body, a catheter tube fitted to a front end of the catheter body, an elastic valve fitted inside the catheter body, and a hollow plug slidably fitted inside the catheter body. The catheter tube, the elastic valve, and the plug are aligned in this order. A connector inserted from a proximal end of the catheter pushes the plug, and the plug presses the elastic valve open.

17 Claims, 4 Drawing Sheets

INDWELLING CATHETER

BACKGROUND OF THE INVENTION

1. Field of the Invention

This invention relates to an indwelling catheter for use in artificial dialysis, fluid infusion, or blood infusion, and more particularly, to an indwelling catheter which avoids backflow of blood outside the catheter when the needle is inserted/removed and allows a connector to be connected thereto with very small force, reducing load to a patient.

2. Description of the Related Art

U.S. Pat. No. 5,911,710 discloses an art related to an indwelling catheter. The indwelling catheter disclosed is a medical insertion device for introducing an elongated tube into a blood vessel and manipulating the tube while maintaining hemostasis. The indwelling catheter has a sheath housing and a shuttle housing. A sheath valve is fitted inside the sheath housing. A shuttle tube is provided in the shuttle housing. When the shuttle housing is pushed forward, the shuttle tube makes the sheath valve open. The use of this indwelling catheter allows tube manipulation while maintaining hemostasis.

SUMMARY OF THE INVENTION

The above indwelling catheter has a hemostatic valve provided in the vicinity of an insertion opening of the shuttle housing for securely maintaining hemostasis in the shuttle housing. When a tube for a drip injection or the like is connected thereto, secured hemostasis is required between the tube and the shuttle housing using the hemostatic valve prior to commencing the opening operation of the sheath valve. The operation of inserting the tube into the hemostatic valve induces a great resistance force, causing the patient much discomfort. The series of operations are complicated, inviting operational errors.

This invention was made to solve the above problems, and has an object of providing an indwelling catheter with good maneuverability, securely maintaining hemostasis in a catheter body with an easy operation.

An indwelling catheter according to a first aspect of this invention comprises: a hollow catheter body; a catheter tube fitted to a front end of the catheter body; an elastic valve fitted inside the catheter body; and a hollow plug slidably fitted inside the catheter body. The catheter tube, the elastic valve, and the plug are coaxially aligned in this order. A connector inserted from a proximal end of the catheter pushes the plug, and the plug presses the elastic valve open.

To introduce the indwelling catheter of this invention into the body of a patient, a needle is inserted from a proximal end of the catheter body to protrude the tip of the needle out from a front end of the catheter tube. The needle presses the elastic valve open, closely contacting with the valve, thereby securely providing hemostasis. The removal of the needle makes the elastic valve close, so that hemostasis is maintained until a drip tube or the like is connected. The connector for connecting a drip tube or the like, when inserted from the proximal end of the catheter body, presses the rear end of the plug with its front end, sliding the plug forward. Then the front end of the plug presses the elastic valve open, maintaining homeostasis and easily providing connection between the drip tube or the like and the indwelling catheter.

An indwelling catheter according to a second aspect of this invention has a biasing means for biasing the plug in a direction opposite to the elastic valve. The biasing means comprises a coil spring or a bellows.

In the indwelling catheter according to the second aspect, the removal of the connector makes the plug return to its original position by the biasing means, making the elastic valve automatically close, and thereby providing hemostasis. Thus the exchange of a drip tube or the like does not require a special operation for hemostasis. This facilitates the exchange of a drip tube or the like.

DETAILED DESCRIPTION OF THE PREFERRED EMBODIMENTS

With reference to FIGS. 1 to 4, a first embodiment of this invention will be described in detail below.

Figure 1:
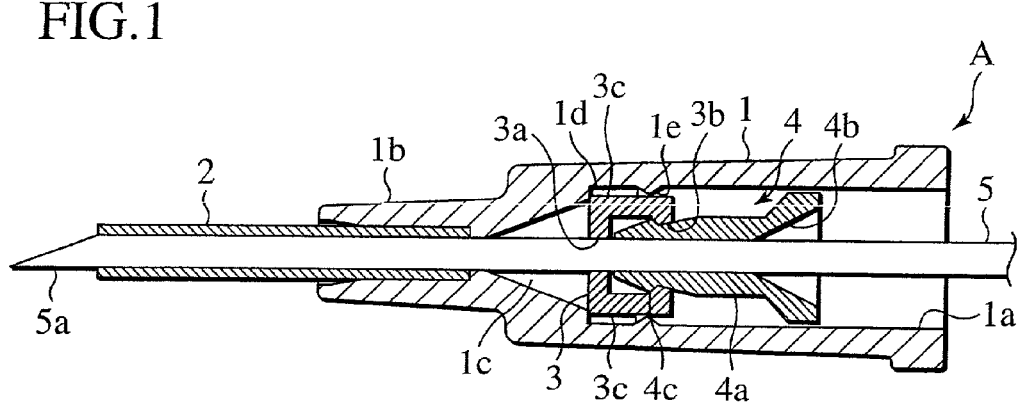
FIG. 1 is a longitudinal cross-sectional view of an indwelling catheter according to a first embodiment of this invention, being ready for insertion into the body of a patient.

An indwelling catheter A according to the first embodiment of this invention has, as shown in FIG. 1, a hollow catheter body 1, a catheter tube 2 fitted into a tube holder 1*b* provided at a distal end of the catheter body 1, an elastic valve 3 fitted inside the catheter body 1, and a hollow plug 4 slidably fitted inside the catheter body 1. The catheter tube 2, the elastic valve 3, and the plug 4 are coaxially aligned in this order.

The catheter body 1 is made from resin or a like material, and has a tubular shape. An inner surface 1*a* is tapered toward the distal end, with a gradually reduced diameter.

The catheter body 1 is preferably of a transparent or semi-transparent material so as to show the interior, enabling checking of movement inside.

The catheter tube 2 is made from resin such as polyamide, and is press-fitted into the tube holder 1b which communicates at its proximal end with the inside of the catheter body 1.

It is preferred that a lubricating coating is provided to the entirety or part of the catheter tube 2 so as to reduce resistance caused by insertion through skin or into a blood vessel.

The elastic valve 3 is of a generally tubular shape, having a closed front surface. The front surface centrally has an openable/closable valve aperture 3a. At an inner surface of a rear opening of the valve 3, an annular protrusion 3b to engage the plug 4 is provided.

The valve aperture 3a is closed watertight when the plug 4 and the needle 5 are not inserted therethrough, providing hemostasis. With the plug 4 inserted therethrough, the valve aperture 3a expands forward and opens, providing communication between the catheter tube 2 and the rear of the catheter body 1.

The annular protrusion 3b protrudes inwardly so as to slidably contact with an outer periphery of the plug 4. The protrusion 3b engages a shoulder 4c provided at a distal end of the plug 4 so as to slidably prevent the dislocation of the plug 4.

A plurality of gaps 3c is defined between an outer periphery of the elastic valve 3 and the inner surface 1a of the catheter body 1. Distal and proximal spaces divided by the elastic valve 3 communicate with each other through the gaps 3c. Thus the elastic valve 3 slides smoothly with air passing through the gaps 3c.

The plug 4 is made from resin or a like material, and has an inner passageway. The plug 4 has a tubular portion 4a, a conical flange 4b connected to the rear end of the tubular portion 4a, and the shoulder 4c protruding from an outer periphery of the tubular portion 4a.

A front end of the tubular portion 4a is chamfered to facilitate its penetration into the valve aperture 3a of the elastic valve 3, and is slidably supported by the annular protrusion 3b of the elastic valve 3.

The conical flange 4b has a conical inner surface so as to facilitate insertion of the needle 5 thereinto. The peripheral surface of the flange 4b contacts the inner surface 1a of the catheter body 1 and serves to provide stability to the plug 4 and maintain the coaxial position with respect to the catheter tube 2.

The indwelling catheter A of this embodiment is prepared for use in such a state as shown in FIG. 1 with the front end of the needle 5 protruding from the front end of the catheter tube 2. In this state, the needle 5 penetrates through the elastic valve 3, providing water-tight connection therebetween, and thereby preventing leakage of blood.

Figure 2:
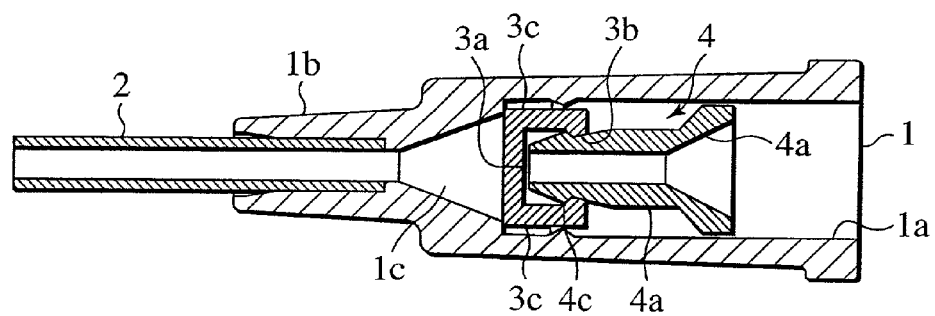
FIG. 2 is a longitudinal cross-sectional view of the indwelling catheter of FIG. 1 with a needle removed.

The indwelling catheter A in this state is inserted into the body of a patient. Then, as shown in FIG. 2, the needle 5 is removed with the tube 2 retained in the body of the patient. The elastic valve 3, being retained in position by an annular protrusion 1e, still remains in the catheter body 1 when the needle 5 is removed, being closed to maintain hemostasis.

Figure 3:
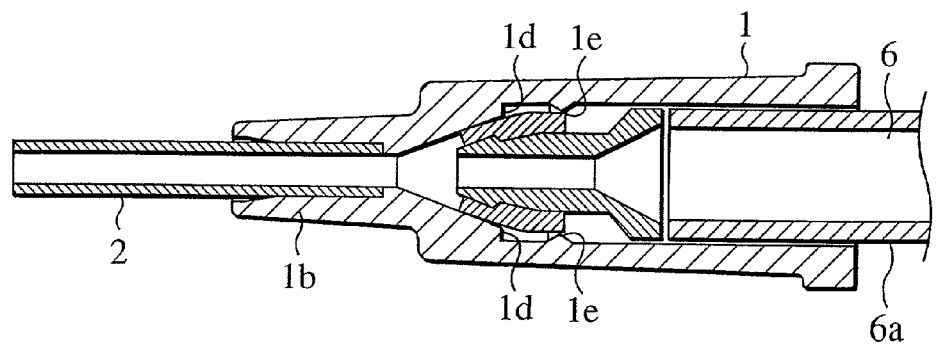
FIG. 3 is a longitudinal cross-sectional view of the indwelling catheter of FIG. 2 with a connector connected thereto.
Figure 4:
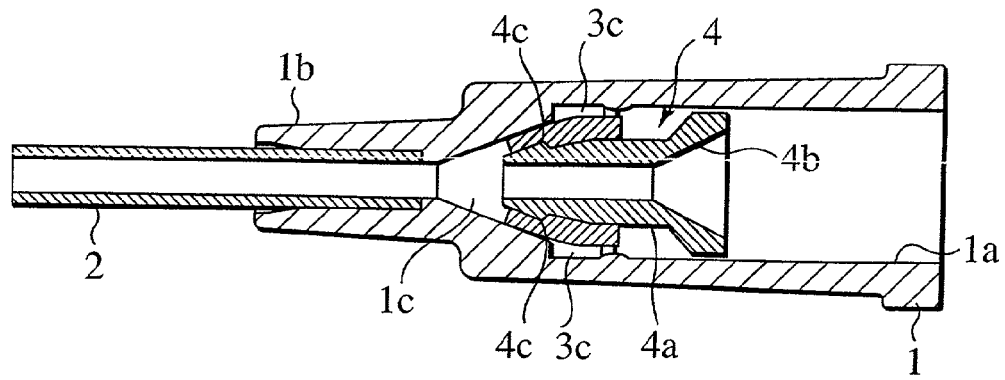
FIG. 4 is a longitudinal cross-sectional view of the indwelling catheter of FIG. 3 with the connecter removed.
Figure 5:
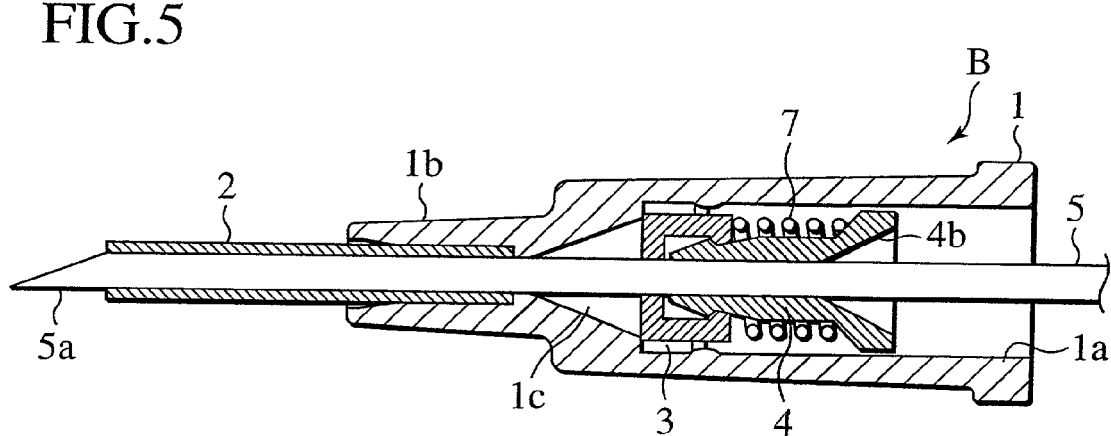
FIG. 5 is a longitudinal cross-sectional view of an indwelling catheter according to a second embodiment of this invention, being ready for insertion into the body of a patient.
Figure 6:
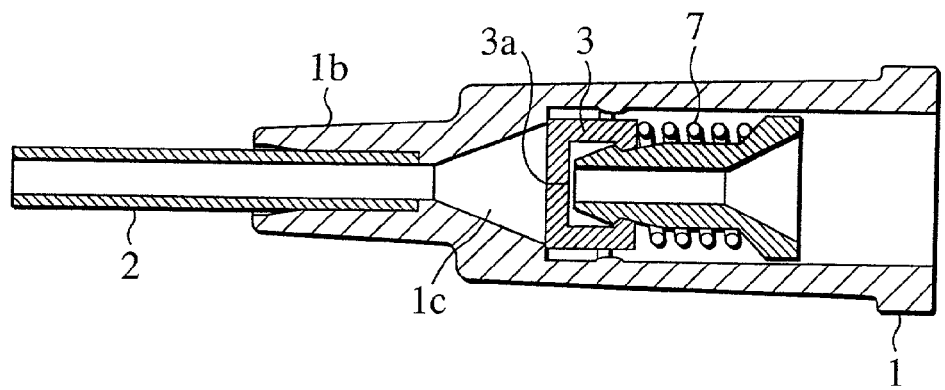
FIG. 6 is a longitudinal cross-sectional view of the indwelling catheter of FIG. 5 with a needle removed.

Then, the connector 6 is inserted from the rear end of the catheter body 1. When pressed into the catheter body 1, the connector 6 pushes at its front end the plug 4. The plug 4 thus slides forward to press at its front end the valve aperture 3a of the elastic valve 3 open. The elastic valve 3 is then pressed against the inner surface of a tapered cavity 1c of the catheter body 1 as shown in FIG. 3, and stops its movement, thus providing communication between the catheter tube 2 and a tube for a drip or the like. The tapered inner surface 1a of the catheter body 1 allows for smooth insertion of the connector 6 and tight contact between an outer surface 6a of the connector 6 and the inner surface 1a through press fitting. The plug 4 is brought into close contact with the elastic valve 3, and the outer surface 6a of the connector 6 is brought into close contact with the inner surface 1a of the catheter body 1, securely providing hemostasis.

With reference to FIGS. 5 to 8, a second embodiment of this invention will be described. In these figures, elements substantially identical with those in the first embodiment are referred to with the same reference numerals. Different or new elements are referred to with new reference numerals.

An indwelling catheter B according to the second embodiment has the structure identical to that of the indwelling catheter A, and further includes a coil spring 7 biasing a plug 4 in a direction opposite to an elastic valve 3. The coil spring 7 is made from a resilient material and is fitted between the elastic valve 3 and the plug 4.

Figure 7:
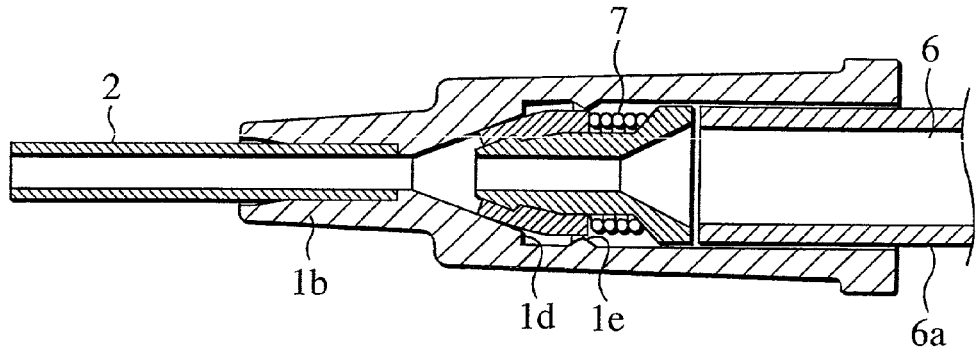
FIG. 7 is a longitudinal cross-sectional view of the indwelling catheter of FIG. 6 with a connector connected thereto.

A connector 6 is inserted from the rear of a catheter body 1 to press the plug 4 against the biasing force of the coil spring 7. The front end of the plug 4 then penetrates into a valve aperture 3a of the elastic valve 3, providing connection between a catheter tube 2 and a drip tube or the like as shown in FIG. 7.

Figure 8:
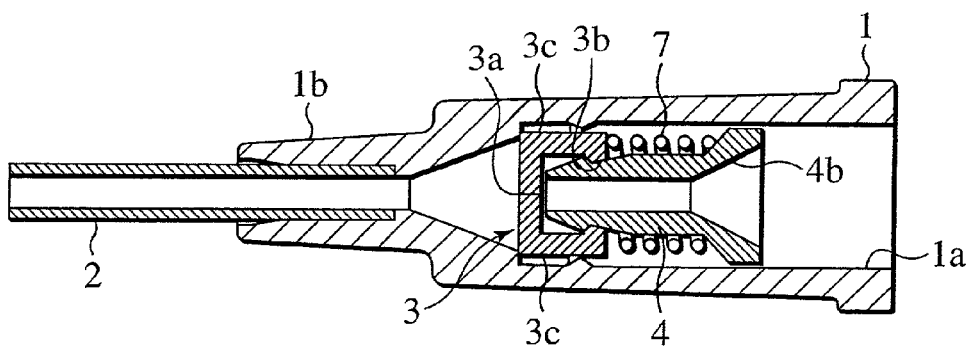
FIG. 8 is a longitudinal cross-sectional view of the indwelling catheter of FIG. 7 with the connecter removed.
Figure 9:
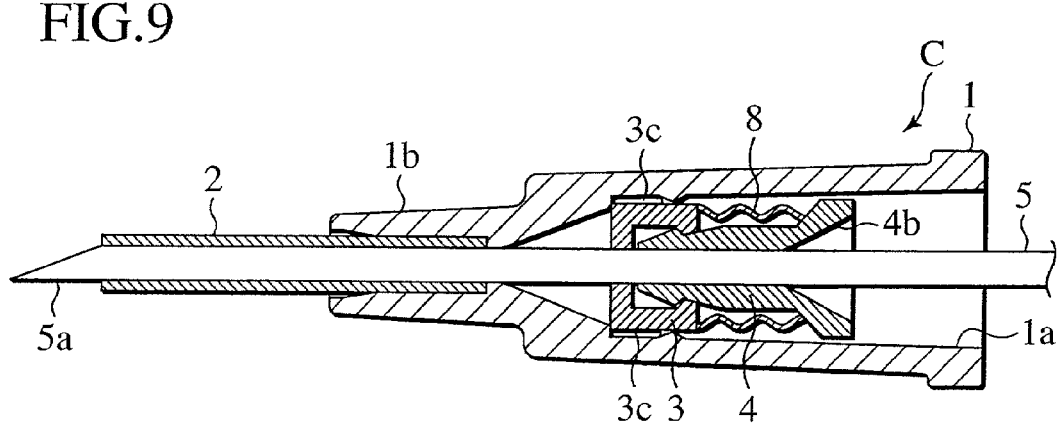
FIG. 9 is a longitudinal cross-sectional view of an indwelling catheter according to a third embodiment of this invention, being ready for insertion into the body of a patient.
Figure 10:
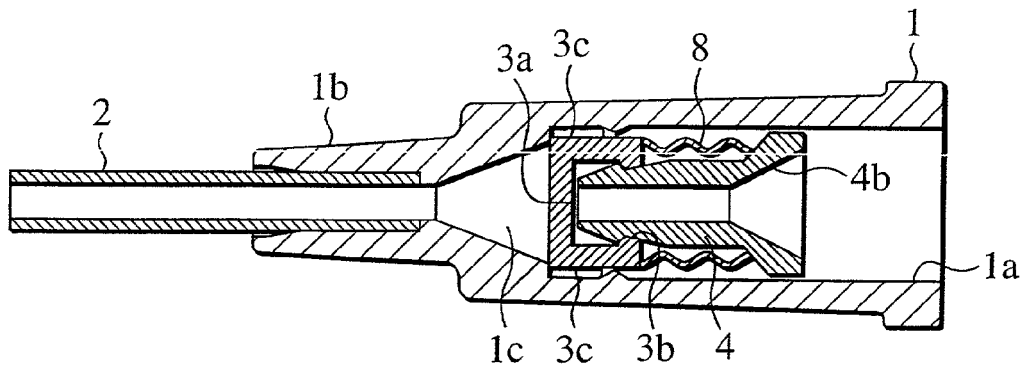
FIG. 10 is a longitudinal cross-sectional view of the indwelling catheter of FIG. 9 with a needle removed.

Then, the connector 6 is removed, and the plug 4 is returned to its original position by the biasing force of the coil spring 7 as shown in FIG. 8. The elastic valve 3 is thus closed, providing hemostasis. That is, the removal of the connector 6 does not require a special operation for hemostasis, resulting in hemostasis being reliably maintained.

With reference to FIGS. 9 to 12, a third embodiment of this invention will be described. In these figures, elements substantially identical with those in the first embodiment are referred to with the same reference numerals. Different or new elements are referred to with new reference numerals.

An indwelling catheter C according to the third embodiment has the structure identical to that of the indwelling catheter B, and has a bellows 8 in place of the coil spring 7 for biasing a plug 4 in a direction opposite to an elastic valve 3. The bellows 8 is made from a resilient material and is fitted between the elastic valve 3 and the plug 4.

Figure 11:
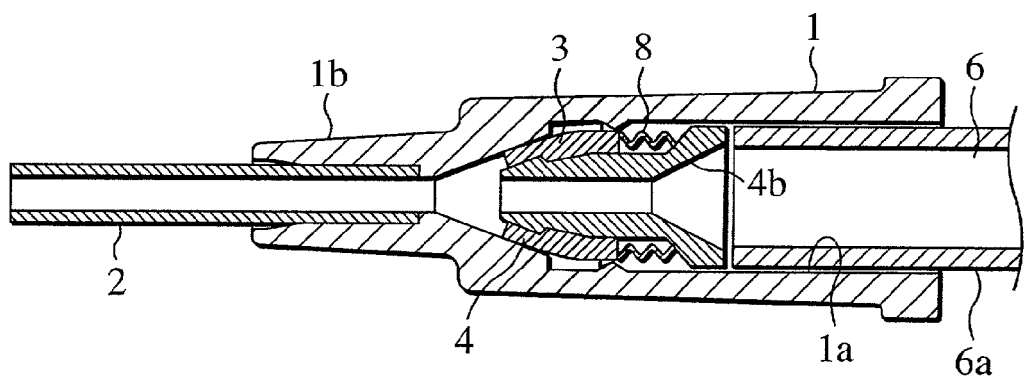
FIG. 11 is a longitudinal cross-sectional view of the indwelling catheter of FIG. 10 with a connector connected thereto.

A connector 6 is inserted from the rear of a catheter body 1 to press the plug 4 against the biasing force of the bellows 8. The front end of the plug 4 then penetrates into a valve aperture 3a of the elastic valve 3, providing connection between a catheter tube 2 and a drip tube or the like as shown in FIG. 11.

Figure 12:
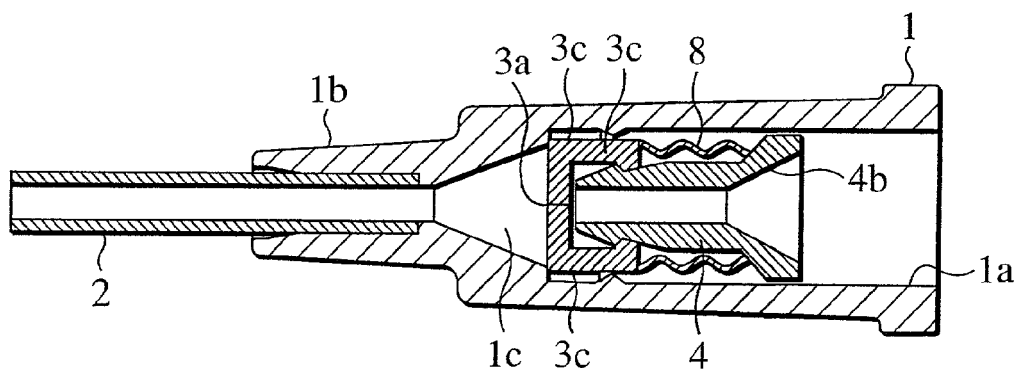
FIG. 12 is a longitudinal cross-sectional view of the indwelling catheter of FIG. 11 with the connecter removed.

Then the connector 6 is removed, and the plug 4 is returned to its original position by the biasing force of the bellows 8 as shown in FIG. 12. The elastic valve 3 is thus closed, providing hemostasis. That is, the removal of the connector 6 does not require a special operation for hemostasis, resulting in hemostasis being securely maintained.

The preferred embodiments of this invention described above are not meant to be limiting. A person with ordinary skill in the art may change or modify the embodiments to implement this invention, based on the above disclosure.

What is claimed is:

1. An indwelling catheter, comprising:
   a hollow catheter body having a front end and a rear end, wherein the rear end has a structure configured to receive and connect with a connector inserted from outside of the rear end;
   a catheter tube fitted to the front end;
   an elastic valve fitted inside the catheter body; and
   a hollow plug slidably fitted inside the catheter body, the plug having a structure configured to allow insertion of a needle from a rear end through the catheter tube and to directly contact and be pressed by the inserted connector so as to open the elastic valve;

wherein, the catheter tube, the elastic valve and the hollow plug are aligned in this order, and the elastic valve has an annular protrusion, and the plug has a shoulder slidably engaging the annular protrusion, whereby the plug is prevented from slipping out form the elastic valve.

2. An indwelling catheter as set forth in claim 1, wherein the catheter body has an inner surface having a tapered shape.

3. An indwelling catheter as set forth in claim 1, wherein one or more gaps are provided between the elastic valve and the catheter body to provide an air passage.

4. An indwelling catheter as set forth in claim 1, wherein the plug is prevented from slipping out from inside the catheter body.

5. An indwelling catheter as set forth in claim 1, wherein the plug is slidably fitted to the elastic valve.

6. An indwelling catheter as set forth in claim 1, further comprising a biasing means fitted outside the plug, the biasing means biasing the plug in a direction opposite to the elastic valve.

7. An indwelling catheter as set forth in claim 6, wherein the biasing means comprises a bellow made of a resilient material.

8. An indwelling catheter as set forth in claim 6, wherein the biasing means comprises a spring coil made of a resilient material.

9. An indwelling catheter as set forth in claim 1, wherein the catheter body is integrally formed.

10. An indwelling catheter, comprising:

a hollow catheter body having a chamber at a rear portion thereof;

a catheter tube fitted to a front end of the catheter body;

an elastic valve fitted inside the catheter body;

a hollow plug slidably fitted inside the catheter body, the plug having a structure configured to allow insertion of a needle from a rear end through the catheter tube;

wherein the catheter tube, the elastic valve and the hollow plug are aligned in this order;

a connector inserted from a rear end of the catheter body into the chamber to push the hollow plug forward so that the hollow plug presses the elastic valve into an open position; and a coil spring disposed between the elastic valve and the hollow plug to exert a force on the elastic valve and the hollow plug to move them apart, wherein the elastic valve has an annular protrusion and the hollow plug has a shoulder which engages with the annular protrusion to retain the hollow plug within the rear opening.

11. An indwelling catheter, comprising:

a hollow catheter body having a front end and a rear end, wherein the rear end has a structure defining a rear opening extending into the catheter body to receive and contact with a connector inserted into the rear opening;

a catheter tube fitted to the front end of the catheter body;

an elastic valve fitted inside the catheter body;

a hollow plug slidably fitted inside the catheter body, the plug having a structure configured to allow insertion of a needle from a rear end through the catheter tube;

wherein, the catheter tube, the elastic valve and the hollow plug are aligned in this order; and a connector inserted from a proximal end of the catheter body into the rear opening so that an end portion of the connector abuts the rear end of the plug within the rear opening of the catheter body to push the plug forward so as to press the elastic valve open, wherein the elastic valve has an annular protrusion, and the plug has a shoulder slidably engaging the annular protrusion, whereby the plug is prevented from slipping out from the elastic valve.

12. An indwelling catheter as set forth in claim 11, wherein the rear opening has an inner surface that is tapered toward one end of the catheter body.

13. An indwelling catheter as set forth in claim 11, wherein one or more gaps are provided between the elastic valve and the catheter body to provide an air passage.

14. An indwelling catheter as set forth in claim 11, wherein the plug is prevented from slipping out from inside the catheter body.

15. An indwelling catheter as set forth in claim 11, wherein the plug is slidably fitted to the elastic valve.

16. An indwelling catheter as set forth in claim 11, further comprising a biasing means fitted outside the plug, the biasing means biasing the plug in a direction opposite to the elastic valve.

17. An indwelling catheter as set forth in claim 16, wherein the biasing means comprises a bellow or a spring coil made of a resilient material.

* * * * *